United States Patent
Jonas

(10) Patent No.: US 12,334,194 B2
(45) Date of Patent: Jun. 17, 2025

(54) DEEP IMITATION LEARNING FOR MOLECULAR INVERSE PROBLEMS

(71) Applicant: University of Chicago, Chicago, IL (US)

(72) Inventor: Eric Jonas, Chicago, IL (US)

(73) Assignee: The University of Chicago, Chicago, IL (US)

( * ) Notice: Subject to any disclaimer, the term of this patent is extended or adjusted under 35 U.S.C. 154(b) by 514 days.

(21) Appl. No.: 17/773,647

(22) PCT Filed: Nov. 3, 2020

(86) PCT No.: PCT/US2020/058685
§ 371 (c)(1),
(2) Date: May 2, 2022

(87) PCT Pub. No.: WO2021/091883
PCT Pub. Date: May 14, 2021

(65) Prior Publication Data
US 2022/0383989 A1  Dec. 1, 2022

Related U.S. Application Data

(60) Provisional application No. 62/930,325, filed on Nov. 4, 2019.

(51) Int. Cl.
*G16C 20/30* (2019.01)
*G16C 20/20* (2019.01)
*G16C 20/70* (2019.01)

(52) U.S. Cl.
CPC .............. *G16C 20/30* (2019.02); *G16C 20/20* (2019.02); *G16C 20/70* (2019.02)

(58) Field of Classification Search
CPC ........ G16C 20/00; G16C 20/20; G16C 20/30; G16C 20/40; G16C 20/70; G16C 20/80;
(Continued)

(56) References Cited

U.S. PATENT DOCUMENTS

2013/0095566 A1   4/2013   Oltvai et al.
2015/0300968 A1*  10/2015  Bae .................. G16B 15/10
                                                    324/309
(Continued)

FOREIGN PATENT DOCUMENTS

WO   2019229036 A1   12/2019

OTHER PUBLICATIONS

Li et al., "Multi-objective de novo drug design with conditional graph generative model," Journal of Cheminformatics, Jul. 24, 2018. (Year: 2018).*

(Continued)

*Primary Examiner* — Son T Le
*Assistant Examiner* — Matthew W. Baca
(74) *Attorney, Agent, or Firm* — Armstrong Teasdale LLP

(57) ABSTRACT

A method of determining a molecular structure of a compound includes obtaining a known molecular formula of the compound based on at least one of an observed spectrum and stoichiometric calculations. Edges that meet per-vertex constraints of the molecular formula are determined, and a plurality of candidate structures is generated based on the determined edges. The plurality of candidate structures are evaluated, and one candidate structure of the plurality of candidate structures is determined as the molecular structure of the compound based on the evaluation of the plurality of candidate structures.

20 Claims, 15 Drawing Sheets
(8 of 15 Drawing Sheet(s) Filed in Color)

(58) Field of Classification Search
CPC ...... G06N 3/044; G06N 3/0455; G06N 3/092; G06N 3/09; G06N 3/091; G06N 3/02; G06N 3/08; G06N 7/01; G06N 20/20; G06F 30/27; G16B 15/00; G16B 15/30; G01N 24/00; G01N 24/087
See application file for complete search history.

(56) References Cited

U.S. PATENT DOCUMENTS

| | | |
|---|---|---|
| 2017/0032078 A1* | 2/2017 | Stelzer .................. G16C 20/60 |
| 2019/0073433 A1 | 3/2019 | Thompson et al. |
| 2019/0294757 A1 | 9/2019 | Prozuments et al. |

OTHER PUBLICATIONS

Sun et al., "Deeply AggreVaTeD: Differentiable Imitation Learning for Sequential Prediction" Proceedings of the 34th International Conference on Machine Learning, PMLR 70:3309-3318, 2017. (Year: 2017).*

PCT International Search Report and Written Opinion for Patent Application PCT/US2020/058685 mailed Jan. 27, 2021; 18 pp.

Jonas, Eric, "Deep Imitation Learning for Molecular Inverse Problems," Department of Computer Science; University of Chicago; available at https://papers.nips.cc/paper/2019/file/b0bef4c9a6e50d43880191492d4fc827-Paper.pdf; last visited Apr. 29, 2022; 11 pp.

* cited by examiner

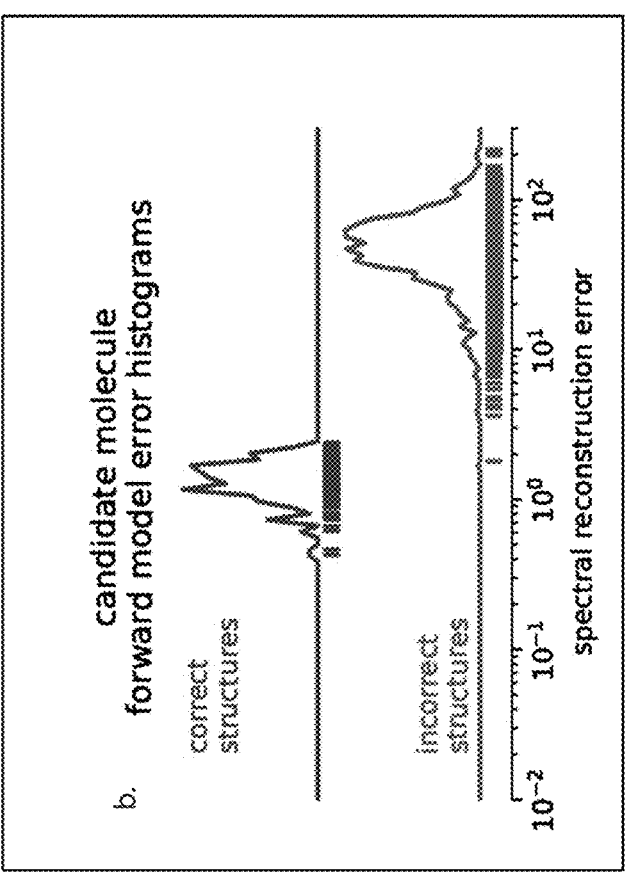
FIG. 7B
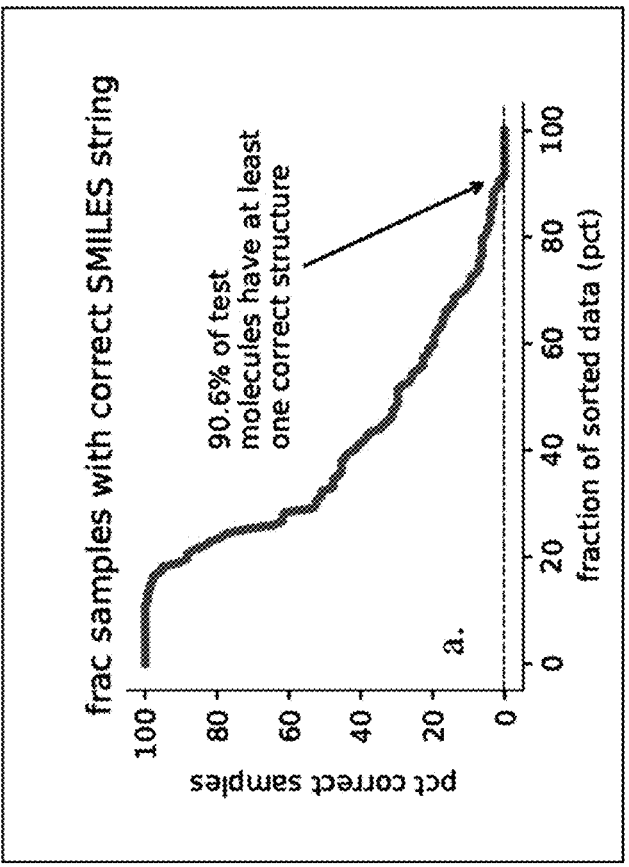
FIG. 7A
FIG. 7C

DEEP IMITATION LEARNING FOR MOLECULAR INVERSE PROBLEMS

CROSS-REFERENCE TO RELATED APPLICATION

This application is a U.S. National Phase Application of International Patent Application No. PCT/US2020/058685, filed Nov. 3, 2020, which claims priority to U.S. Provisional Application Ser. No. 62/930,325, filed on Nov. 4, 2019, each of which is hereby incorporated by reference in its entirety.

BACKGROUND OF THE DISCLOSURE

Early work on function approximation and machine learning techniques for inverse problems, including neural networks, focused primarily on one-dimensional problems. More recent work has focused on enhancing and accelerating various sparse linear recovery problems. These approaches can show superior performance to traditional reconstruction and inversion methods but a large fraction of this may be due to learning better data-driven regularization.

Deep learning methods for graphs have attracted considerable interest over the past several years, beginning with graph convolutional kernels and continuing to the present. Many of these advances have been applied to chemical problems, including trying to accurately estimate whole molecule properties, finding latent embeddings of molecules in continuous spaces and optimizing molecules to have particular scalar properties. These approaches have focused on exploiting the latent space recovered by GANs and variational autoencoders. Crucially these molecule generation approaches have largely focused on optimizing a single scalar property by optimizing in a learned latent space, which had made constraints like the precise number and elements of atoms difficult.

Other approaches have attempted to sequentially construct graphs piecemeal using RNNs and deep Q-learning, however, disclosed herein is an oracle policy that is known to be correct: the ability to explicitly calculate subisomorphism between $E_{k+1} = e_{ijc} \cup E_k$ and the final $G_K$. This results in a reduction to learning to imitate the oracle, a substantially easier problem.

The systems and methods described herein extend various approaches (e.g., recent work on structured prediction via imitation learning, sometimes termed learning to search) to dense connected graphs via an explicit subisomorphism oracle.

Finally, the use of machine learning methods for chemical inverse problems is historic, especially with regards to other types of spectroscopy, such as mass spec. One of the first expert systems, DENDRAL, was conceived in the early 1960s to elucidate chemical structures from mass spectroscopy data, which fractures elements and measures the charge/mass ratio of the subsequent fragments. Commercial software exists to perform chemical structure determination from two-dimensional NMR data, a richer but substantially slower form of NMR data acquisition, which measures both chemical shift values and scalar coupling constants between nuclei, which can directly inform bond structure. Accordingly, there is a need for faster, more efficient, more accurate, and more reliable structure discovery, and the embodiments described herein resolve at least these known deficiencies. The 1-D NMR focus described herein dramatically accelerates the structure discovery process.

BRIEF DESCRIPTION OF THE DISCLOSURE

In one aspect, a method of determining a molecular structure of a compound includes obtaining a known molecular formula of the compound based on at least one of an observed spectrum and stoichiometric calculations. Edges that meet per-vertex constraints of the molecular formula are determined, and a plurality of candidate structures is generated based on the determined edges. The plurality of candidate structures are evaluated, and one candidate structure of the plurality of candidate structures is determined as the molecular structure of the compound based on the evaluation of the plurality of candidate structures.

In another aspect, the present disclosure is directed to a computing device system for determining a molecular structure of a compound. The computing device includes a processor and a memory. The memory includes instructions that program the processor to: obtain a known molecular formula of the compound based on an observed spectrum of the compound, determine edges that meet per-vertex constraints of the molecular formula, generate a plurality of candidate structures based on the determined edges, evaluate the plurality of candidate structures, and determine one candidate structure of the plurality of candidate structures as the molecular structure of the compound based on the evaluation of the plurality of candidate structures.

In yet another aspect, the present disclosure is directed to a system for determining a molecular structure of a compound. The system includes a spectroscopic instrument configured to generate an observed spectrum of the compound, and a computing device communicatively coupled to the spectroscopic instrument. The computing device includes a processor and a memory. The memory includes instructions that program the processor to: obtain a known molecular formula of the compound based on an observed spectrum of the compound, determine edges that meet per-vertex constraints of the molecular formula, generate a plurality of candidate structures based on the determined edges, evaluate the plurality of candidate structures, and determine one candidate structure of the plurality of candidate structures as the molecular structure of the compound based on the evaluation of the plurality of candidate structures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The embodiments described herein may be better understood by referring to the following description in conjunction with the accompanying drawings.

FIG. 7A is an exemplary embodiment of a graphical depiction of candidate molecule distribution in accordance with the present disclosure. FIG. 7B is an exemplary embodiment of a graphical depiction of reconstruction error distribution in accordance with the present disclosure. FIG. 7C is an exemplary embodiment of a graphical depiction of jitter and reference noise data in accordance with the present disclosure.

DETAILED DESCRIPTION OF THE DISCLOSURE

Figure 1A:
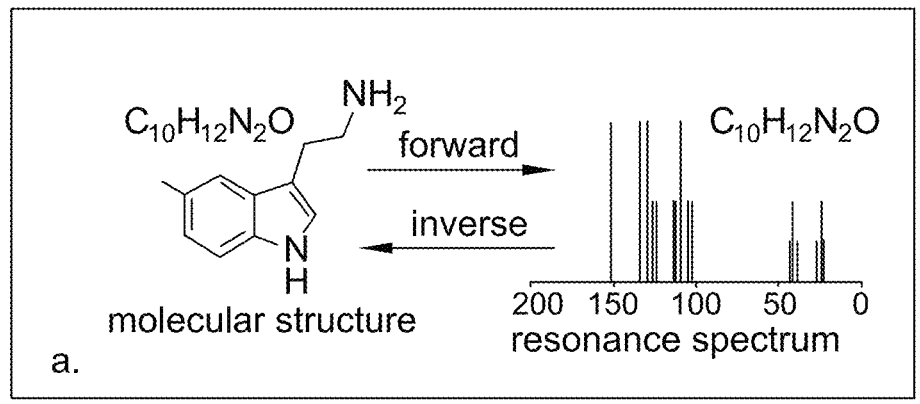
FIG. 1A is an exemplary embodiment of a graphical depiction of a molecular structure and its resonance spectrum in accordance with the present disclosure.

Many measurement modalities arise from well-understood physical processes and result in information-rich but difficult-to-interpret data which still requires laborious human interpretation. In nuclear magnetic resonance (NMR) spectroscopy, the observed spectrum of a molecule provides a distinguishing fingerprint of its bond structure. As disclosed herein, the resulting inverse problem is solved: given a molecular formula and a spectrum, the chemical structure is inferred. The correct molecular structure can be quickly computed for a wide variety of molecules, and failed method outcomes are detected with reasonable certainty. Here, the problem is treated as a graph-structured prediction where, armed with per-vertex information on a subset of the vertices, the edges and edge types are inferred. The problem is framed as a Markov decision process (MDP) and incrementally constructs molecules one bond at a time, training a deep neural network via imitation learning, thus imitating a subisomorphic oracle which knows which remaining bonds are correct. Instead of predicting the whole structure, the structure is built incrementally with sequential bond formation, which is an imitation learning problem fully-observed for deterministic actions. The methods provided are fast, accurate, and among the first chemical-graph generation approaches to exploit per-vertex information and generate graphs with vertex constraints. The methods disclosed herein provide automation of molecular structure identification and active learning for spectroscopy.

INTRODUCTION

Understanding the molecular structure of unknown and novel substances is a long-standing problem in chemistry, and is frequently addressed via spectroscopic techniques, which measure how materials interact with electromagnetic radiation. One type of spectroscopy, nuclear magnetic resonance spectroscopy (NMR) measures properties about individual nuclei in the molecule. This information can be used to determine the molecular structure, and indeed this is a common, if laborious, exercise taught to organic chemistry students.

Although not usually conceived of as such, this is actually an inverse problem. Inverse problems are problems where it is attempted to invert a known forward model $y=f(x)$ to make inferences about the unobserved x from measurements y. Inverse problems are at the heart of many important measurement modalities, including computational photography, medical imaging, and microscopy. In these cases, the measurement model is often linear, that is $f(x)=Ax$, and the recovered x is a vector in a high-dimensional vector space. Crucially, A is both linear and well-known, as a result of extensive hardware engineering and calibration.

Nonlinear inverse problems have a non-linear forward model f, and structured inverse problems impose additional structural constraints on the recovered x, like being a graph or a permutation matrix. Spectroscopy is an example of this sort of problem, where it is desired to recover the graph structure of a given molecule from its spectroscopic measurements. The model f is known very well, in the case of NMR due to decades of expertise in quantum physics and computational chemistry, especially techniques like Density Functional Theory (DFT).

Figure 8:
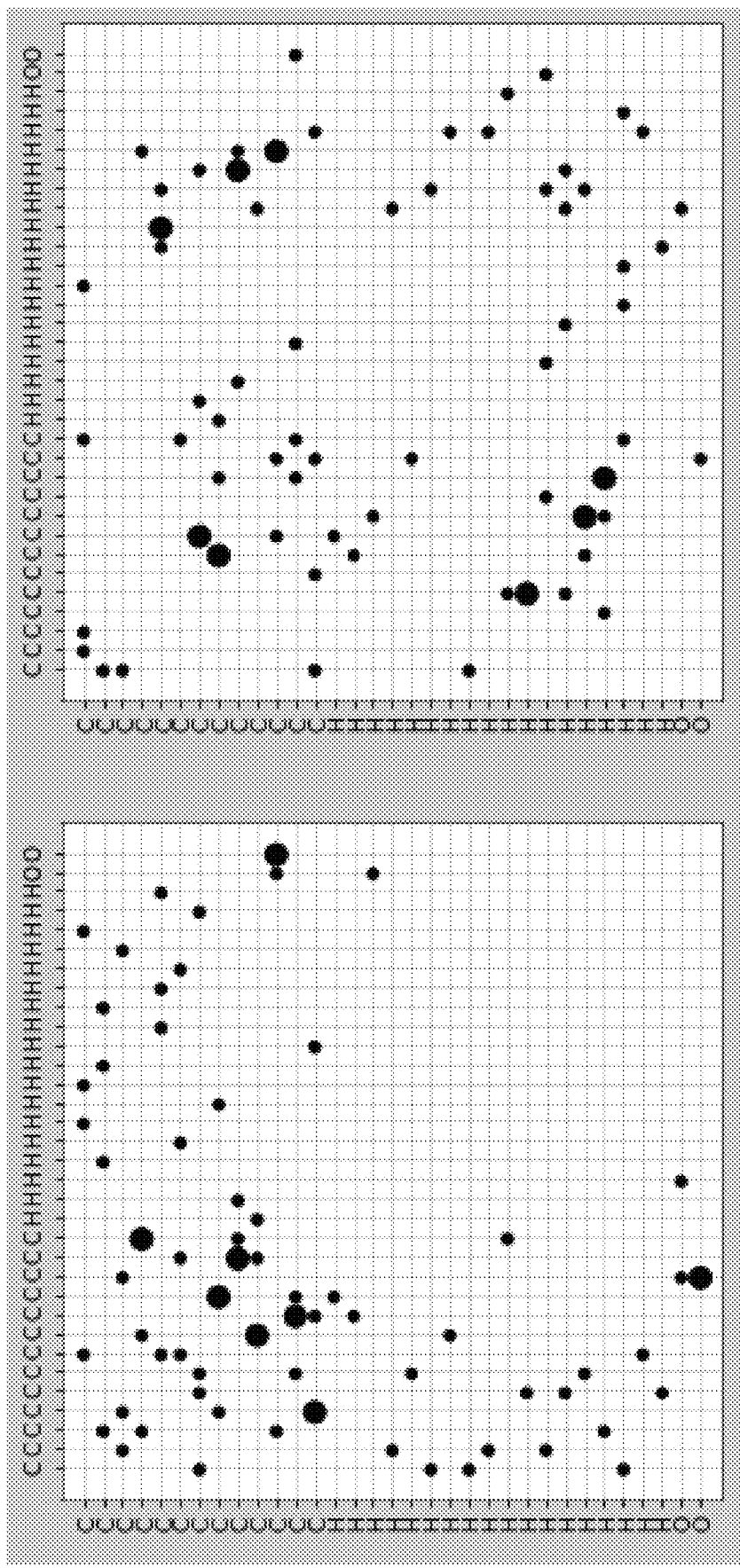
FIG. 8 is an exemplary embodiment of a graphical depiction of graph isomorphism in accordance with the present disclosure.

Here the inverse problem to be tackled is structured as follows: Given a collection of per-atom (vertex) measurements, the molecular structure (labeled edges) may be recovered. Note that a single, correct graph is sought—unlike recent work in using ML techniques for molecules, here there is one true, correct edge set (up to isomorphism) to be found. FIG. 8 shows a two-graph example that are the same, thus showing that graph isomorphism makes it challenging to directly optimize over predicted graph structures. The problem is formulated as a Markov decision process, and uses imitation learning to train a deep neural network to sequentially place new bonds until the molecule is complete. The availability of a fast approximate forward model (this model is used herein throughout the disclosure and is treated as correct, thus the "approximate" designation is hereinafter dropped) f enables a rapid check to see if the recovered structure matches experimental data, allowing more confidence in the veracity of there covered structure.

As discussed herein, relevant graph-theoretic connections to chemistry and NMR spectroscopy are briefly reviewed, the sequential problem setup is explained, the dataset is presented, and the resulting Markov decision process (MDP) is solved via imitation learning. Both synthetic and real data are evaluated, showing that the resulting problem is invertible, is reasonably well-posed in the face of input data perturbations, and crucially performs well on experimentally-observed data for many molecules. Further, improvements to be made are assessed to both the forward model f and the inverse that are described herein.

Basic Chemistry. A molecule consists of a collection of atoms of various elements, with certain types of "bonds" between those atoms, thus corresponding to the definitions provided herein below.

A molecule is:
1. A collection of vertices (atoms) $V=\{v_i\}$, each vertex having a known color (that is, corresponding to a particular element) and maximum vertex degree, corresponding to the valence of that element.
2. A set of edges $E=\{e_{ij}\}$ between the vertices $(v_i, v_j) \in V$ each with an associated edge label c corresponding to their bond order. The bond orders of interest are labeled $\{1, 1.5, 2, 3\}$ corresponding to single, aromatic, double, and triple bonds.
3. A graph $G=(V, E)$ which is connected, simple, and obeys a color-degree relationship by which the weights of the edges connected to a vertex $v_i$ almost always sum to a known value dependent on that vertices' color.

The measurement technique primarily used herein, NMR spectroscopy, allows observation of various per-vertex properties, $P(v_i)$, which can then be featurized. Note only $P(v_i)$ is observed for a subset of nuclei, and the set of all of these observations will be referred to as P.

Figure 1B:
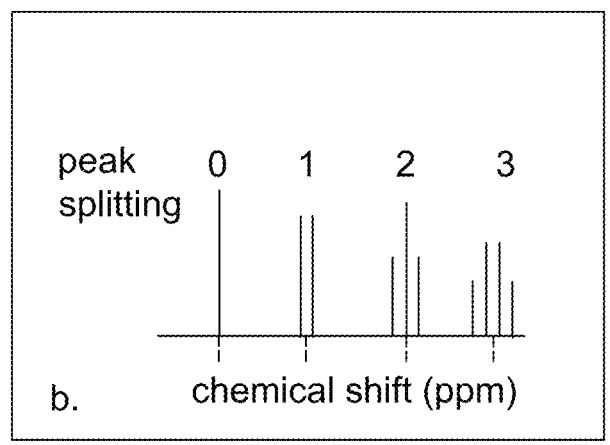
FIG. 1B is an exemplary embodiment of a graphical depiction of chemical shift in accordance with the present disclosure.

A known molecular formula, such as $C_8H_{10}N_4O_2$, is obtained via stoichiometric calculations or alternative techniques such as mass spectroscopy, UV-vis, IR, near-IR, FTIR, and x-ray crystallography, for example. In some embodiments, the known molecular formula is found via an observed spectrum obtained from techniques including NMR spectroscopy, mass spectroscopy, IR spectroscopy, UV-vis spectroscopy, atomic adsorption spectroscopy, emission spectroscopy, photoluminescence spectroscopy, Ramen spectroscopy, attenuated total reflectance Fourier-transform infrared spectroscopy (ATR-FTIR), EPR spectroscopy, and Circular dichroism spectroscopy. FIG. 1A shows that the forward problem is how to compute the spectrum of a molecule (right) given its structure (left). Spectroscopists seek to solve the corresponding inverse problem, working backward from spectra towards the generating structure. FIG. 1B shows various properties measured in a spectrum, including the chemical shift value and the degree to which each peak is split into multiplets. In the application of NMR spectroscopy, there are two sources of per-vertex information measured (FIG. 1B) in an experiment: a unique per-nucleus resonance frequency, the chemical shift, that arises as a function of the local electronic environment, and peak splitting, which results from spin-spin coupling between a nucleus and its neighbors. As disclosed herein, $^{13}C$ spectroscopy is focused on, and thus only these properties for carbon atoms are observed; all other nuclei yield no spectroscopic information. In this case, the splitting then reflects the number of adjacent hydrogens bonded to the carbon. The problem ultimately is as follows: based upon a collection of per-vertex measurements, what is the label (if any) of the edge $e_{ij}$ between all vertex pairs $(v_i, v_j)$. In embodiments that use mass spec, m/z ratios and peak intensities are used instead of chemical shift and peak splitting. In some mass spec based embodiments, a pre-processing step is used to articulate and identify the fragments beforehand. In such embodiments, as the molecules are broken down, weights are used to determine which peaks go with which atoms.

Sequential Molecule Assembly Via Imitation Learning

The problem is formulated as a Markov decision process (MDP), where the process begins with a known set of vertices V and their observed properties P, and sequentially adds bonds until the molecule is connected and all per-vertex constraints are met. Let $G_k=(V, P, E_k)$ represent the kth state of the model, with k existing edges $E_k$, $k \in [0, \ldots, K]$. The model seeks to learn the function $p(e_{k+1}=e_{i,j,c}|E_k, V, P)$ assigning a probability to each possible new edge between $v_i$ and $v_{ij}$ (with label c) and in $G_{k+1}$.

To generate a single molecule (given spectral observations P and per-vertex information V) an empty edge set $E_0$ is created and sequentially sampled from $E_k \sim p(e_{i,j,c}|E_k, V, P)$ until the correct number of edges have been placed necessary to satisfy all the valence constraints. This resulting edge set (molecule) is called a candidate structure. For a given spectrum P, this process can be repeated N times, generating N (potentially different) candidate structures, $\{E_K^{(i)}\}_{i=1}^N$. It is possible then to evaluate the quality of these candidate structures by measuring how close their predicted spectra $P_i=f(E_K^{(i)})$ are to the true observations P, that is, $$E_{predicted} = \operatorname{argmin}_i \|f(E_K^{(i)}) - P\|^2$$

Figure 12:
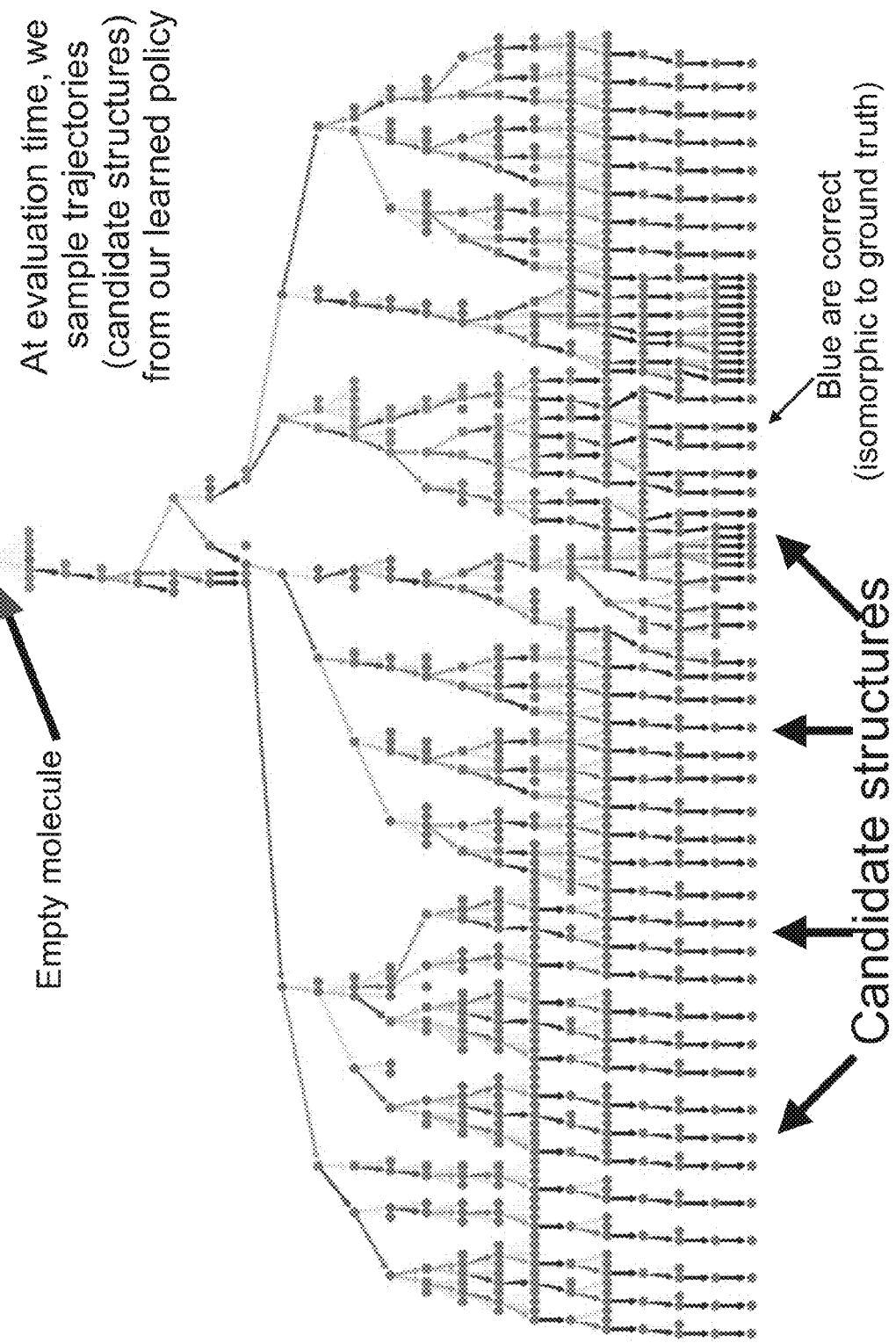
FIG. 12 is an exemplary embodiment of a graphical depiction of generated molecules in accordance with the present disclosure.

The sequential molecule generation process can produce a large number of candidates but the presence of the fast forward model can rapidly filter out incorrect answers. FIG. 12 shows a graphical representation of the molecule generation as a tree structure.

Figures 2A, 2B:
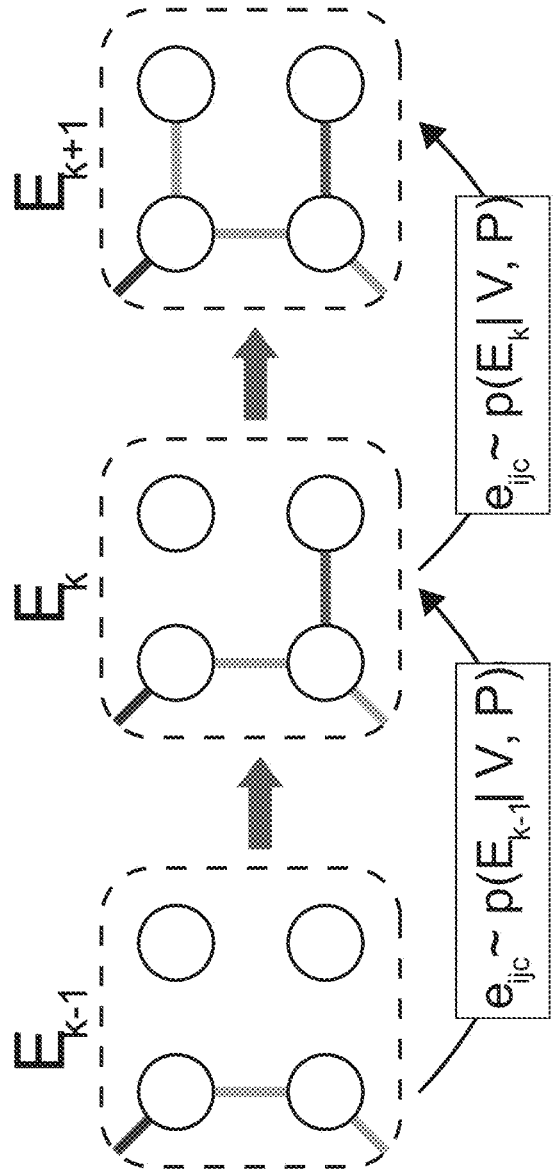
FIG. 2A is an exemplary embodiment of a graphical depiction of input in accordance with the present disclosure.
FIG. 2B is an exemplary embodiment of a graphical depiction of sequential construction in accordance with the present disclosure.
Figure 2C:
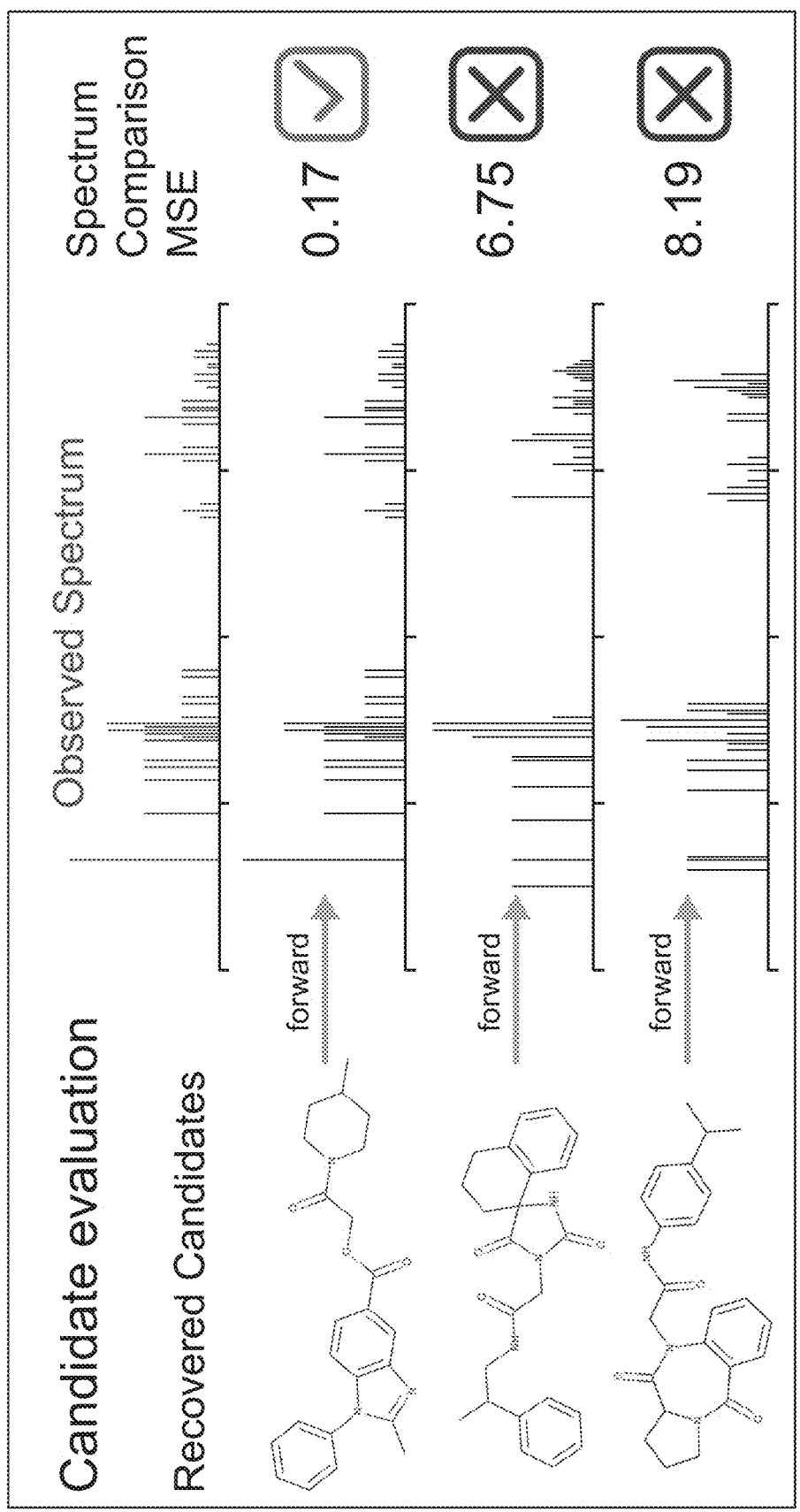
FIG. 2C is an exemplary embodiment of a graphical depiction of candidate evaluation in accordance with the present disclosure.

Imitation learning. For any partially completed molecule $G_k=(V, P, E_k)$ the single correct edge set $E_K$ is sought. The ability to efficiently compute graph subisomorphism as an oracle is utilized—at training time the individual edges $e_{i,j,c}$ are computed that can be added to $E_k \cup \{e_{i,j,c}\}$ such that $G_{k+1}$ would still be subisomorphic to $G_K$ (details of this subisomorphism calculation are provided herein elsewhere). According to FIG. 2A-C: FIG. 2A shows the input is a molecular formula indicating the number of atoms (vertices) of each element (color) along with per-vertex properties P measured for a subset of those vertices (in this case, carbon nuclei). FIG. 2B shows sequential construction of a molecule by sampling the next edge (i, j) and edge label c conditioned on the existing edge set as well as vertices V and vertex properties P. FIG. 2C shows that the result is a sampled collection of candidate molecules, which can then be passed back through the forward model to compute their spectra, and validate against the true (observed) spectrum.

Figure 3:
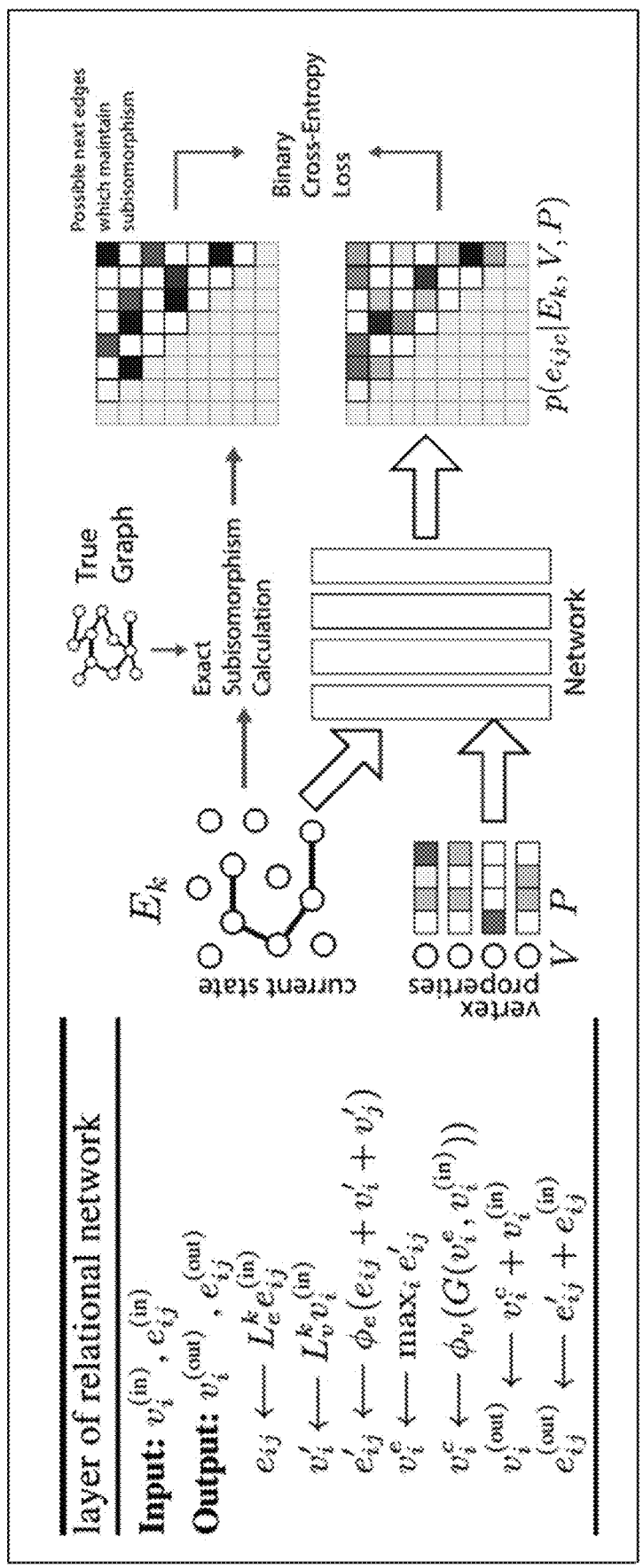
FIG. 3 is an exemplary embodiment of a graphical depiction of a layer of a relational network in accordance with the present disclosure.

A large number of candidate $(G_k, E_{k+1})$ training pairs are generated, and fit to a function approximator to $p(e_{i,j,c}|E_k, V_p)$. FIG. 3 shows each layer k of the network transforms per-vertex $v^{(in)}$ and per-edge features $e^{(in)}$ into per-vertex $v^{(out)}$ and per-edge $e^{(out)}$ output features. At train time, true graphs are taken, a subset of edges are randomly deleted, and it is exactly compute which single edges could be added back into the graph and maintain subisomorphism. the binary cross-entropy loss is minimized between the output of the network and this matrix of possible next edges. To generate these training pairs, a known molecule $G_K$ with observed properties P is taken and d edges are randomly deleted yielding state $G_{K-d}$ (see FIG. 3). Note this is a crucial difference between the problem and previous molecule generation work: at each point when assembling a molecule, there is a finite, known set of valid next edges, as the model seeks a single correct structure.

There are many ways to sample the number of deleted edges d and a pathological choice may yield distributional shift issues, where sequentially-assembled molecules during the recovery phase might look significantly different from the training molecules. This was not observed in practice, although adoption of distributional-shift techniques such as SEARN or DAGGER are worth further exploration. Sampling of d was such that the fraction of remaining edges is distributed as a mixture of uniform and beta distributions, $d \sim 0.2 \cdot \text{Unif}(0, 1) + 0.7 \cdot \text{Beta}(3, 3)$.

Dataset. Computing the spectrum from a given complete molecule G requires computationally-expensive quantum-mechanical (DFT) calculations, and there is a paucity of high-quality NMR experimental data available. Learning fast neural-network-based approximations for spectra is leveraged to address this problem. The original fast forward model was trained on a small number of experimentally-available spectra, and then that model was used to synthesize the spectra of a very large number of candidate molecular structures.

Molecular structures were obtained consisting of H, C, O, and N atoms by downloading a large fraction of the public database PubChem. Molecules were selected with no more than 64 atoms total and at most 32 heavy atoms (C, O, and N). This dataset was preprocessed to eliminate excessively small (<5 atoms) rings and excessively large rings (>8 atoms), as well as radicals, as they were absent in the initial dataset that trained the approximate forward model. Care is taken to ensure that no molecule is duplicated in the database, contaminating the train/test split. This leaves 1,268,461 molecules, of which 819,200 are trained on and the test set is drawn from the remainder.

Figure 9:
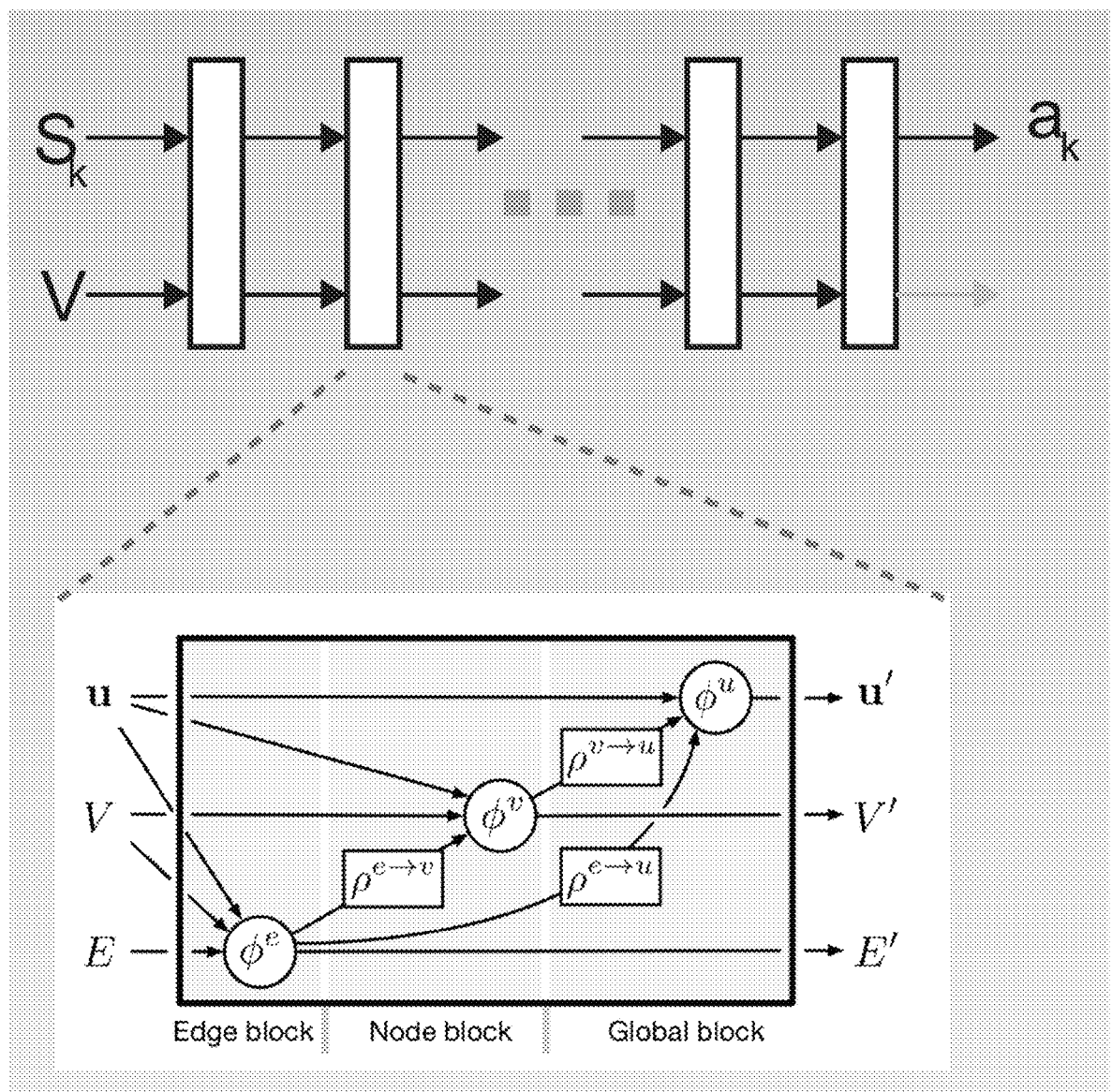
FIG. 9 is an exemplary embodiment of a graphical depiction of a relational network in accordance with the present disclosure.
Figure 10:
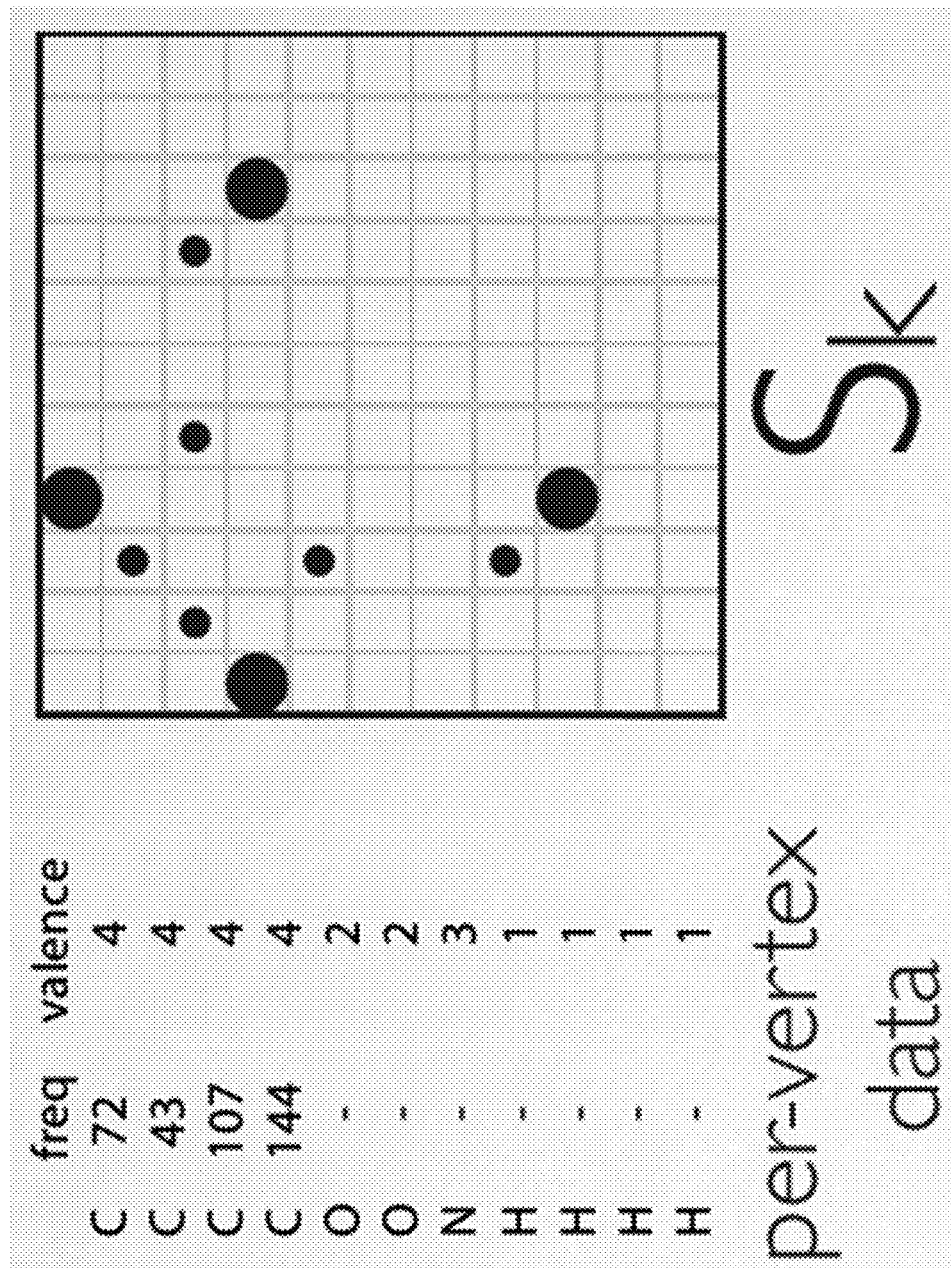
FIG. 10 is an exemplary embodiment of a graphical depiction of inputs for a relational network in accordance with the present disclosure.
Figure 11:
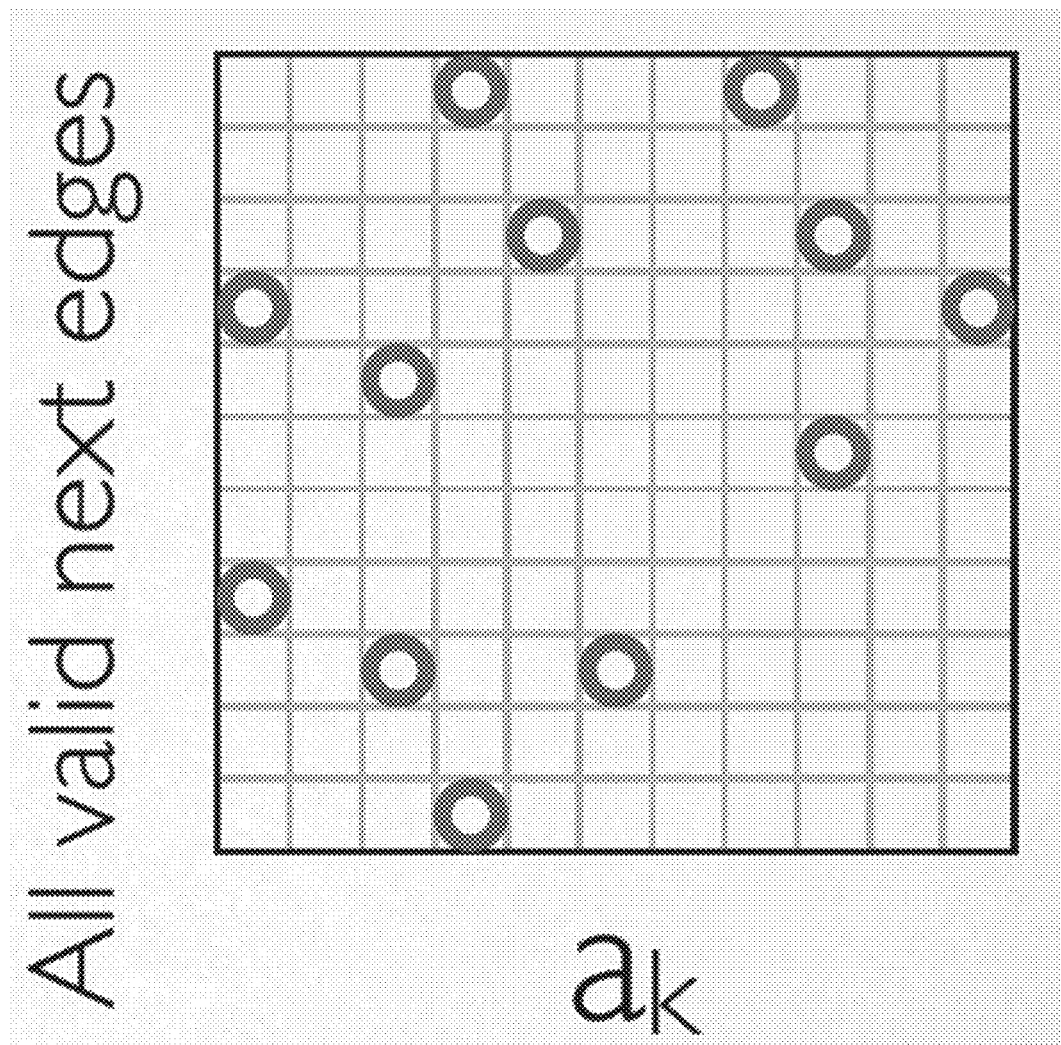
FIG. 11 is an exemplary embodiment of a graphical depiction of an aggregate of all valid next edges associated with a vertex output by a relational network in accordance with the present disclosure.

Network. The network assigns a probability to each possible edge and edge-label given the current partially-competed graph, $p(e_{i,j,c}|E_k, V, P)$. As shown in FIG. 9, the network itself is a cascaded series of layers which combine per-edge and per-vertex information, sometimes called a "relational network". As shown in FIGS. 10 and 11, each layer k of the network transforms per-vertex $v^k$ and per-edge features $e^k$ into pervertex $v^{(k+1)}$ and per-edge $e^{(k+1)}$ output features. The network combines pairwise vector features with the associated edge features $e_{ij}' = \emptyset_e(e_{ij}+v_i'+v_j')$ when computing the next edge feature, and computes an aggregate of all edges associated with a vertex $v_i^e = \max_i e_{ij}'$.

A residual structure was adopted as it was easier to train, as was the $\emptyset_r$, perform batch normalization before ReLu operations. A recurrent GRU cell was found to be the easiest to train efficiently when combining input per-vertex features with the aggregated edge features $G(v_i^e, v_i^{(k)})$. Note the network at no point depends on the ordering of the input per-vertex or per-edge features, thus maintaining permutation-invariance.

The first layer takes in per-vertex properties including element type, typical valence, and others (see below) as well as the experimentally-observed per-vertex measurements for the relevant nuclei, including one-hot-encoded (binned) chemical shift value and peak splitting. the current state of the partially-assembled molecule was also featurized as a one-hot-encoded adjacency matrix, where $e_{i,j,c}^{in}=1$ if there is an edge labeled c between $v_i$ and $v_j$ and 0 otherwise.

32 relational layers were cascaded with an internal feature dimensionality of 256, discarding the final layer's per-vertex information. Each output edge is passed through a final 1024-dimensional fully-connected layer to reduce its dimensionality down to 4 for output outputting a one-hot-encoded edge weight for each of the four possible edge labels. the resulting outputs were normalized to give the final $p(e_{i,j,c}|E_k, V, P)$.

Binary cross-entropy loss training was used between the allowed possible next edges and the predicted edges of the network. Adam was used with a learning rate of $10^{-4}$ and train the network for 100 hours on an nVidia v100 GPU.

Network details. For each input molecule in the training set features were computed that depend on the vertices and their assigned properties (Table 1), per-vertex features which are informative about the current edge state $E_k$ of the partially-assembled molecule $G_k$ (Table 2), and per-edge current edge state features $E_k$ (Table 3).

TABLE 1

Per-vertex features state-independent features

| attribute | description | dimensionality |
|---|---|---|
| atomic number | one-hot encoded (C, N, O) | 3 |
| default valence | one-hot-encoded (1-3) | 3 |
| spectrum | binarized, 64-bins, 0-220 (see below) | 64 |
| observed peak splitting | one-hot encoded (0-3) | 4 |

The observed chemical shift value was one-hot encoded for the nuclei where it is measured into a series of discrete bins (64) over a range of 0-220 ppm. Rather than merely discretizing the shift value, a Gaussian with $\sigma=2$ was discretized allowing for information to be shared between bins. Early experiments revealed this to improve performance.

TABLE 2

Per-vertex state-dependent features.

| attribute | description | dimensionality |
|---|---|---|
| current degree | summed effective edge weight | 1 |
| remaining degree | remaining effective edge weight | 1 |
| remaining degree | remaining degree one-hot encoded [−1.0, 0.0, 1.0, 1.5, 2.0, 2.5, 3.0, 4.0] | 8 |

TABLE 3

Per-edge state-dependent features.

| attribute | description | dimensionality |
|---|---|---|
| edge label | adge label as weight | 1 |
| edge presence | is there an edge here | 1 |
| edge label | one-hot-eacoded edge label [0, 1, 1.5, 2, 3] | 5 |

Calculation of graph subisomorphism. Efficient calculation of graph subisomorphism is a computationally challenging problem, with no known solution for all cases. Fortunately several existing high-quality libraries exist which take advantage of reasonable heuristics and work well in practice. The recently-developed VF2++ algorithm was used herein, implementation of which was found to be nearly twice as fast as existing libraries with substantially better performance on outlier cases. VF2++ only supports labeled vertices, not edges, so each input graph was transformed with labeled edges into a bipartite graph with labeled edge nodes, and subsequently compute subisomorphism. Note that a subisomorphism calculation was performed for every candidate possible next edge in every molecule in a minibatch. At the size and problem complexity exemplified in the embodiments disclosed herein, on average computing the full set of next edges for a molecule takes roughly 10 ms, and with appropriate threading can be done online and does not rate-limit the training process.

Figure 4:
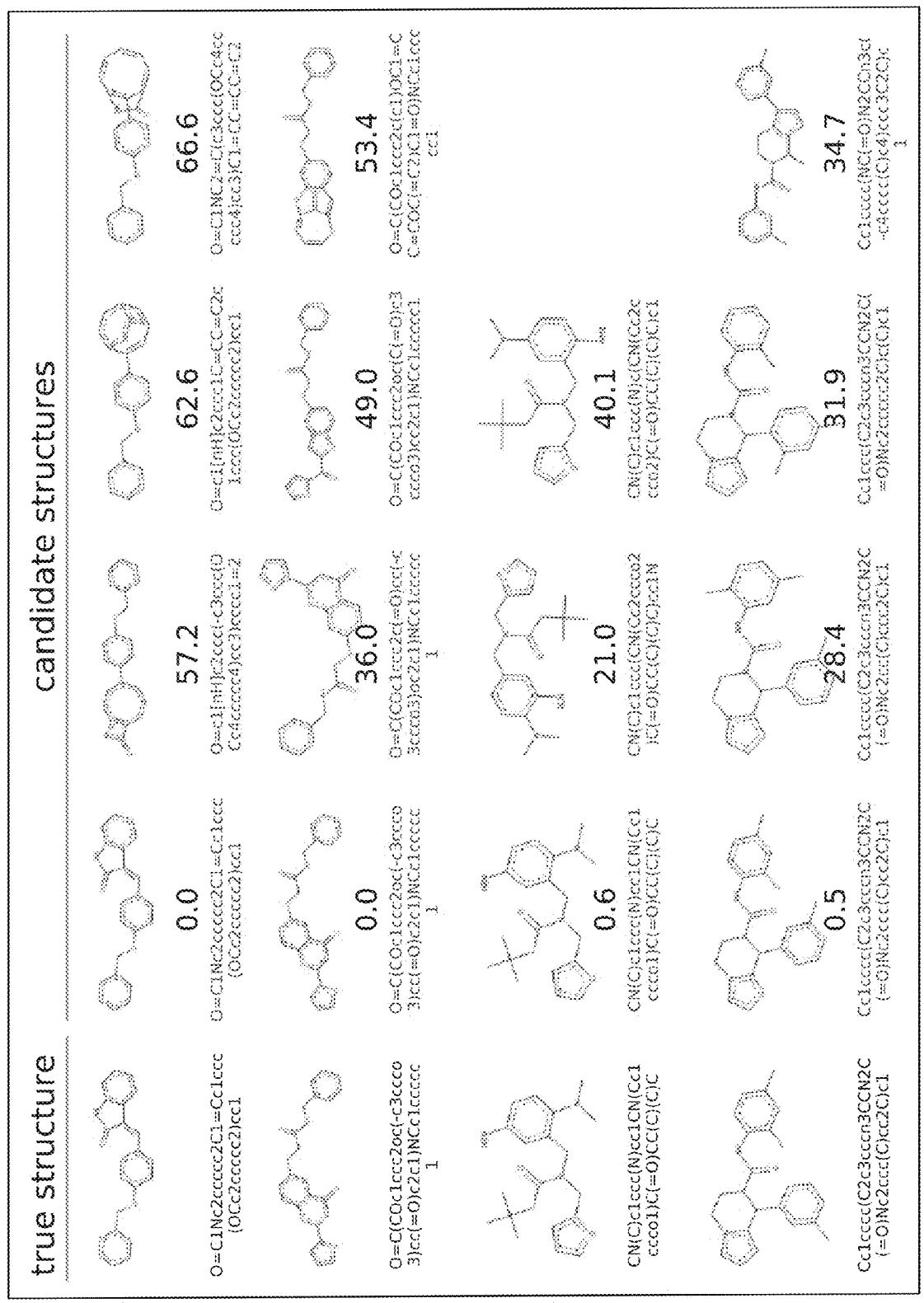
FIG. 4 is an exemplary embodiment of a graphical depiction of correctly recovered structures in accordance with the present disclosure.
Figure 5:
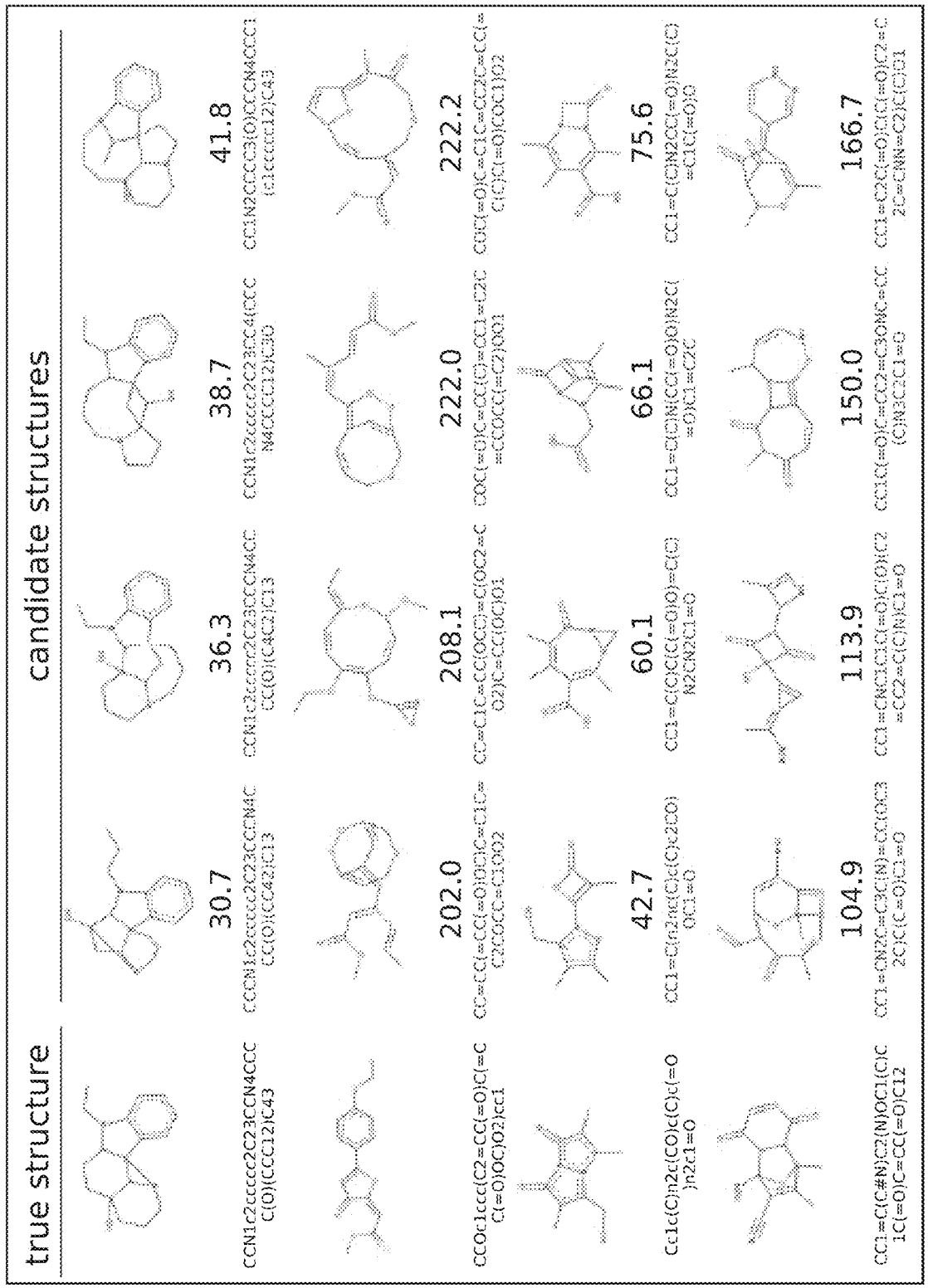
FIG. 5 is an exemplary embodiment of a graphical depiction of incorrectly recovered structures in accordance with the present disclosure.

Example results. Example results are shown in FIG. 4 and FIG. 5. FIG. 4 shows correctly recovered structures on the left. The left-most column is the true structure and associated SMILEs string, and the right are the candidate structures produced by the method disclosed herein, ranked in order of spectral reconstruction error. FIG. 5 shows incorrectly recovered structures on the left. The left-most column is the true structure and associated SMILEs string, and the right are the candidate structures produced by our method, ranked in order of spectral reconstruction error. Note that none of the indicated structures has a low spectral agreement.

Brief overview of the forward model. Extensive use was made of a fast forward model, where a small collection of empirically-measured spectra is used to train a model, the results of which are briefly summarized herein.

Measured experimental spectra for 32538 molecules from NMRShiftDB2 are contributed by a user and are used to train an edge-sensitive (that is, bond-order-aware) graph neural network to encode per-vertex properties, which then uses several feedforward (linear) layers to predict both a mean and a variance for the requested chemical shift. Training proceeded with a variational loss which approximately fits a small Gaussian to the observed data, parameterized by mean and variance. This had the added benefit of making it easier to fit/ignore the outliers in our source-database, of which there were many due to its user-contributed nature.

Ultimately, this model is used to generate the estimated $^{13}C$ chemical shifts for the input data. Only predicted shift mean is used—the confidence interval may be further taken into account for more accurate data augmentation (beyond the simple Gaussian noise model).

Evaluation

The molecule samples candidate structures for a given set of observations using the trained policy, and then checks each of those structures' agreement with the observed data using the fast forward model. this error in reconstruction is called the spectral reconstruction error for candidate edge set $E_K^i$ $$S_e = \|f(E_K^{(i)}) - P\|^2$$

While training, generating graphs with exact isomorphism is attempted—that is, the recovered graph is isomorphic to the observed graph, including all per-vertex properties. This is excessively stringent for evaluation, as the experimental error for chemical shift values can be as high as 1 ppm, thus experimentally a carbon with a shift of 115:2 and a carbon with a shift of 115:9 are indistinguishable. Thus, the definition is relaxed and it is concluded that two molecules are correct if they agree, irrespective of exact shift agreement, according to a canonicalized string representation. Here SMILES strings were used, which are canonical string representations of molecular structure with extensive use in the literature. SMILES strings are a more realistic definition of molecular equivalence. The SMILES generation code in RDKit, a popular Python-based chemistry package, was used.

Inversion, identifiability, noise sensitivity. First ability to simply recover the correct molecular structure given observed data was assessed, operating entirely on simulated data, using the exact spectra produced by the forward model f. This noise-free case represents the best case for the model, and allows assessment of the degree to which the system works at all—that is, the combination of chemical shift data and peak splitting data may be sufficient to uniquely recover molecular structure.

Figure 6:
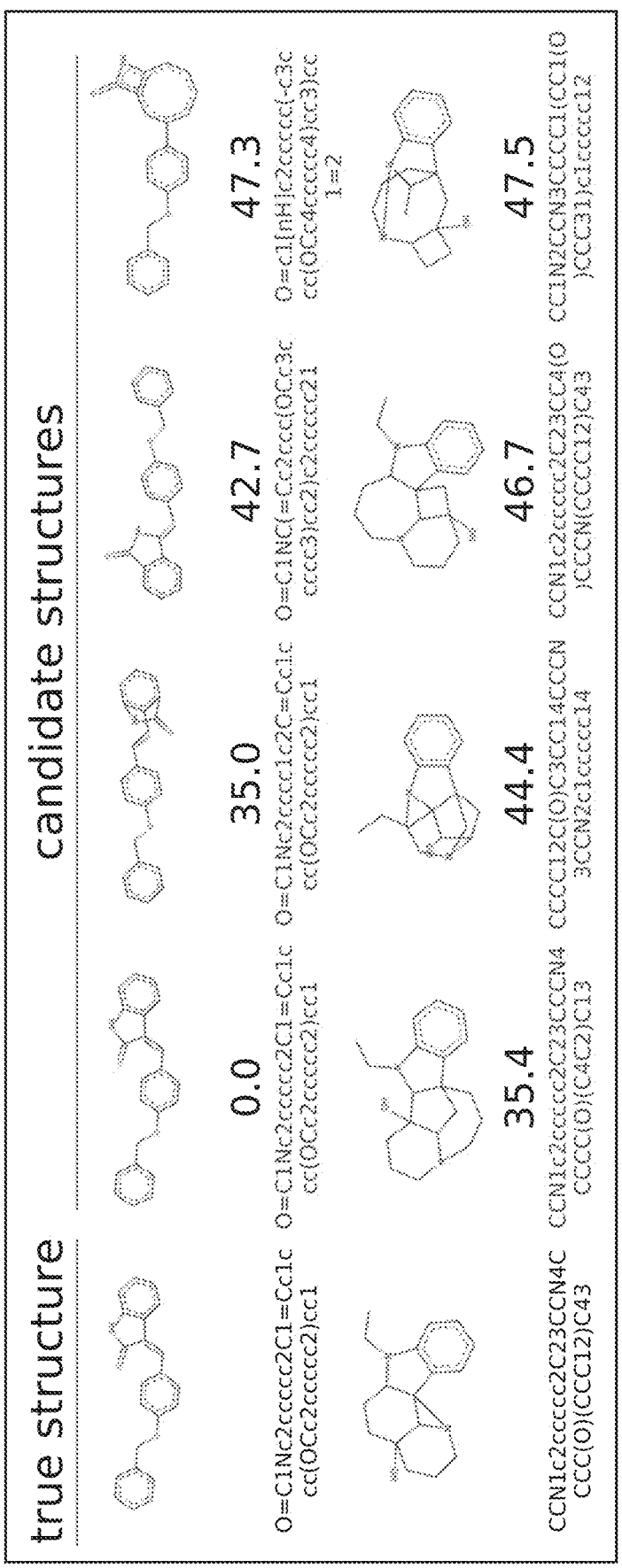
FIG. 6 is an exemplary embodiment of a graphical depiction of example recovered structures in accordance with the present disclosure.

For each spectrum in the test set the model generates 128 candidate structures and measure the fraction which are SMILES-correct. FIG. 6 shows example spectra and recovered molecules, both correct and incorrect (see FIG. 4 and FIG. 5). In FIG. 6, the left-most column is the true structure and associated SMILEs string, and the right columns show the candidate structures produced by the method disclosed herein, ranked in order of spectral reconstruction error (number below). Color indicates correct SMILEs string. The top row shows a molecule for which the correct structure was recovered, and the bottom row is an example of a failure to identify a structure. Since in this case spectral observations computed by the forward model are used, the spectral reconstruction error should be exactly 0.0 for the correct structure, and all incorrect structures have substantially larger spectral errors when passed through the forward model.

For each test molecule, a fraction of the 128 generated candidate models are correct, irrespective of how well the forward model matches. This is a measure of how often the model produces the correct structure, and in the noiseless case is the best case. FIG. 7A-C show synthetic data. FIG. 7A shows a distribution of candidate molecules that are correct, before filtering, for the noiseless case. For 90.6% of the test molecules generated at least one correct structure. FIG. 7B shows a distribution of reconstruction errors for correct and incorrect candidate structures, showing a clear separation. FIG. 7C shows that jitter adds random noise to each shift value independently, whereas reference noise shifts the entire spectrum by a random amount. Models are trained on each class of noise and evaluate on each class of model. The performance as measured by AUC minimally degrades when the model is trained with the equivalent noisy (augmented) data. FIG. 7A shows the fraction of correct candidate structures sorted in decreasing order; it can be seen that 90.6% molecules in the test set have at least one generated structure that is correct. each of these candidate structures is then passed back through the forward model and evaluate the MSE between the observed spectrum for the true molecule and the spectra of the candidates. FIG. 7B shows the distribution of reconstruction error for the correct structures and for the incorrect structures; a clear separation is visible, suggesting the existence of a threshold that can be used to reliably distinguish correct from incorrect structures.

Well-posedness. Inverse problems are often ill-posed in the sense of Hadamard, where the solution can vary wildly with slight perturbations in the input. To evaluate the ill-posedness of the model, again data is generated with the forward model, but these spectra are perturbed at evaluation time via with per-chemical-shift jitter and reference noise.

Per-shift jitter can arise in SNR-limited applications when precise measurement of the chemical shift peak is difficult, modeled here as the addition of Gaussian noise, training with $\sigma=0.5$ and evaluating with $\sigma=\{0.1, 1.0\}$. Reference noise can arise when the reference frequency is mis-calibrated or mis-measured and manifests as an offset applied to all observed chemical shift values. Here this is modeled as a uniform shift on [−2, 2] ppm.

As noise was added to the observed data at evaluation time, in this case the spectral reconstruction error $S_e$ will never be zero—even the candidate structure with the lowest $S_e$ will not match the forward model exactly. A threshold can be set for this reconstruction error, below which a solution will simply not be chosen or suggested—in this case the model is effectively saying "I don't know, none of these candidate structures fit well enough". For a given evaluation set of molecules, this threshold can be varied—when it is very low, only solutions for a small number of molecules may be suggested (but they are more likely to be correct). This threshold can then be varied over the range of values, and compute the resulting area under the curve (AUC). This threshold-based confidence approach is used herein throughout the disclosure.

The model was trained with no noise in the training data, and with training data augmented with just per-shift jitter, and with reference noise and per-shift jitter. The resulting models were evaluated on evaluation datasets with no noise, jitter at two values, and reference noise (FIG. 7C).

From the table in FIG. 7C, training the presence of noise can substantially improve noise robustness, and reference artifacts are more damaging to recovery AUC, even when the model is trained with them. While this model is robust to some classes of perturbations, the precise chemical shift values do matter. Further work includes systematic exploration of this sensitivity.

FIGS. 8-22 further illustrate exemplary embodiments of the approach and methods disclosed herein.

Experimental Data

All previous results have been using spectra generated from the fast forward model described herein, now compared with actual experimentally-measured spectra. NMR-ShiftDB was used for all data. The original forward model was trained on a small number of experimentally-available spectra, and then that model was used to synthesize the spectra of a very large number of molecular structures from PubMed. This gave four different classes of experimental molecules to evaluate: molecules from the train and test sets of the forward model, and molecules whose structures were used in training the inverse network or not.

This performance was evaluated in Table 4. The AUC was measured as the "reconstruction error" threshold was varied, and the accuracy of the top 10%, 20%, and 50% molecules with the lowest reconstruction error were observed.

TABLE 4

Experimental data.

| evaluation data from | | | threshold accuracy | | | | |
|---|---|---|---|---|---|---|---|
| forward | inverse | AUC | 10% | 20% | 50% | top-1 | top-5 |
| train | train | 0.95 | 100.0% | 100.0% | 99.2% | 79.5% | 79.9% |
|  | test | 0.88 | 100.0% | 99.0% | 96.9% | 71.3% | 74.6% |
| test | train | 0.91 | 100.0% | 100.0% | 97.6% | 60.3% | 63.3% |
|  | test | 0.83 | 100.0% | 97.1% | 90.2% | 55.9% | 58.6% |

Table 4 shows evaluation on varying degrees of unseen molecules. "Train" and "test" indicate whether the forward or inverse model was trained on the evaluation set or not. ("test", "test") represent molecules completely unseen at both training and test time, and reflect the most realistic scenario. "threshold accuracy" reflects the SMILES accuracy of the top n % of molecule-prediction matches, by spectra MSE. Top-1 and top-5 are average correctness across the entire dataset of the top-1 and top-5 candidate structures.

For molecules whose structure was never seen by either the approximate forward model or the inverse model, an AUC of 0:83 was achieved and a top-1 accuracy of 55:9%. A $S_e$ threshold can be selected which gives a prediction for 50% of the molecules, and in this case the correct structure was recovered 90:2% of the time.

The other forward/inverse pairings can be used to sanity check these results and understand the relative importance of molecular structure and chemical shift prediction between the forward and the inverse model. Unsurprisingly when the structure was known to both the forward and the inverse model, the best performance is achieved, even when the inverse model never observed the empirical shifts, only the simulated shifts from the forward model. AUC drops by 0.07-0.08 between train and test sets for the inverse model, regardless of whether or not the molecule was in forward model training or test. Similarly, AUC drops by 0.04-0.05 between forward model train and test, regardless of whether the inverse model had seen the molecule or not. This is suggestive of a consistent independent role for both forward model accuracy and inverse model performance, and suggests that improving either will ultimately yield improved reconstruction performance.

DISCUSSION

The capability to reconstruct entire molecular graphs from per-vertex spectroscopic information via deep imitation learning is demonstrated herein. This inverse problem is made viable by the on-line generation of an enormous amount of training data, enabled by the construction of a fast forward model to quickly compute these per-vertex properties, and efficient computation of exact graph subisomorphism.

The approach described herein is very general for molecular spectroscopy problems, and allows for many steps and extensions before complete automation of the process of chemical structure identification. While the approach described herein gives the ability to evaluate the quality of candidate structures (by passing them back through the forward model and computing MSE), this approach is not perfect. Avenues for improvement include both expanding the fraction of molecules confidently predicted and the resulting accuracy.

First, the process begins by focusing on molecules with the four most common organic elements (H, C, O, and N) with extension of the method to other elements occurring subsequently. One challenge is that the accuracy of chemical shift prediction for NMR spectra is less accurate for other important organic elements like S, P, F, and Cl. Even best-in-class density functional theory calculations struggle to accurately compute ab initio chemical shift values for heavier atoms such as metals, and molecules with unusual charge distributions such as radicals.

While focus herein was entirely on $^{13}$C NMR, $^1$H NMR has a substantially higher signal-to-noise ratio (SNR) due to the near-100% natural abundance of the spin-active hydrogen isotope. However, the chemical shift range for hydrogen is substantially smaller (~9 ppm) and much more variable. Nonetheless, a high-quality forward model approximation for hydrogen spectra enables easy incorporation of information into the model and improve performance.

Like the majority of machine learning approaches to chemistry, by focusing entirely on topology substantial geometric effects, both stereochemical and conformational, are ignored. As different stereoisomers can have radically different biological properties, correctly identifying stereoisomerism is an important challenge, especially in natural products chemistry. Incorporating this explicit geometry into both a forward model approximation and an inverse recovery is an important aspect of the systems and methods disclosed herein.

More complex forms of NMR are capable of elucidating more elements of the coupled spin system created by a molecule, giving additional information about atomic bonding. As noted above, this is the basis for the (substantially slower) technique present in 2D NMR. Incorporating this style of data into the models disclosed herein is straightforward, by developing a forward model that accurately predicts the parameters for the full spin Hamiltonian, and has the potential to extend performance to substantially-larger molecules.

Finally, there is tremendous potential in using techniques as disclosed herein to make the spectroscopic process active. As the NMR spectrometer is fully programmable, it may be possible to use the list of uncertain candidate structures to compute successive follow-on experiments to more confidently identify the true structure. This style of active instrumentation will require the existence of very rapid forward and inverse models, including models such as those provided herein.

Figure 13:
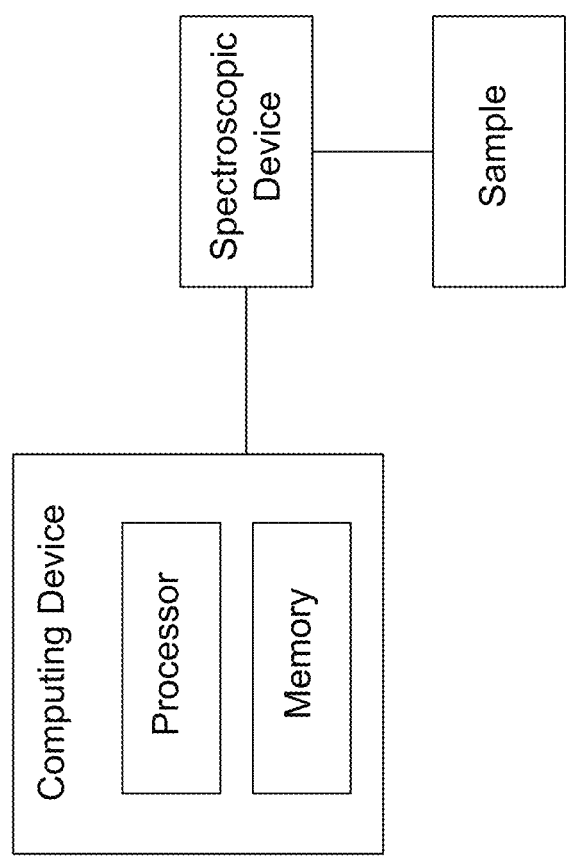
FIG. 13 is an exemplary deep imitation learning system for molecular inverse problems.
Figure 14:
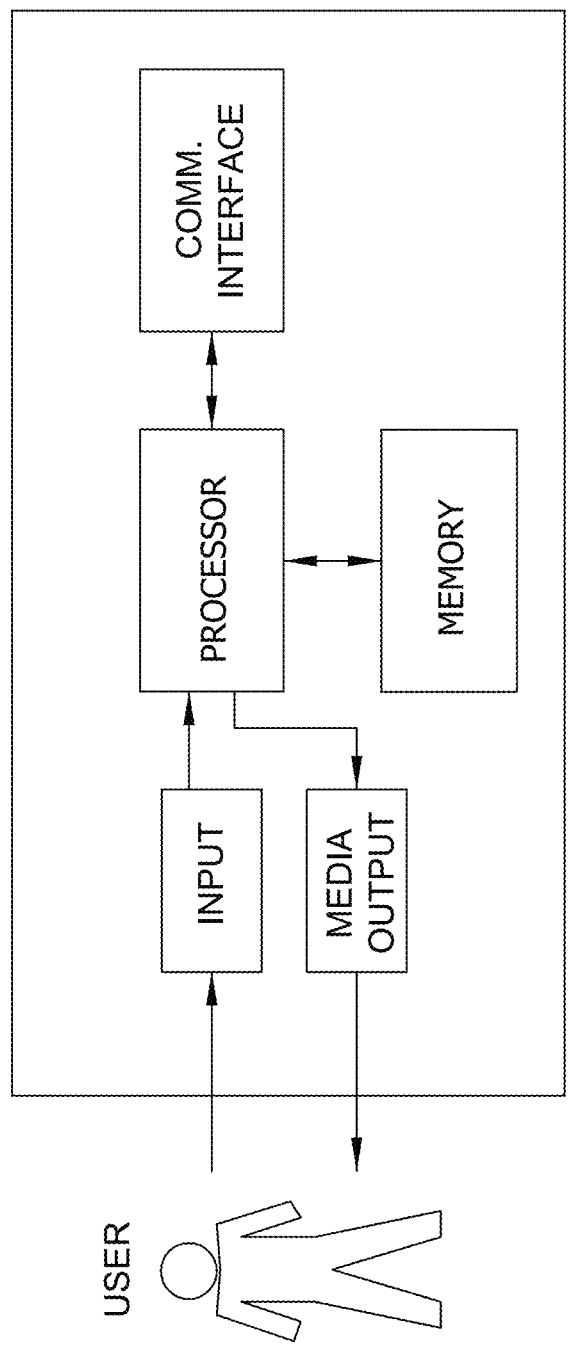
FIG. 14 is an exemplary computing device for use in the system in FIG. 13.

FIG. 13 is an exemplary deep imitation learning system for molecular inverse problems. The system includes a computing device and a spectroscopy device that captures magnetic fields around atomic nuclei of a sample and classifies the imaged object using the techniques described herein. The computing device is communicatively coupled to the spectroscopy device to receive data from the sample. In some embodiments, the computing device controls operation of the spectroscopy device to acquire magnetic resonance data of the sample. Moreover, in some embodiments, the computing device is integrated into the spectroscopy device, while in other embodiments, the computing device is located remote from the spectroscopy device. FIG. 14 is an example computing device for use as the computing device shown in FIG. 13 or may be a separate computing device for deep imitation learning for use in the system of FIG. 13. The computing device includes a processor, a memory, a media output component, an input device, and a communications interface. Other embodiments include different components, additional components, and/or do not include all components shown in FIG. 14.

Some embodiments involve the use of one or more electronic processing or computing devices. As used herein, the terms "processor" and "computer" and related terms, e.g., "processing device," "computing device," and "controller" are not limited to just those integrated circuits referred to in the art as a computer, but broadly refers to a processor, a processing device, a controller, a general purpose central processing unit (CPU), a graphics processing unit (GPU), a microcontroller, a microcomputer, a programmable logic controller (PLC), a reduced instruction set computer (RISC) processor, a field programmable gate array (FPGA), a digital signal processing (DSP) device, an application specific integrated circuit (ASIC), and other programmable circuits or processing devices capable of executing the functions described herein, and these terms are used interchangeably herein. The above embodiments are examples only, and thus are not intended to limit in any way the definition or meaning of the terms processor, processing device, and related terms.

In the embodiments described herein, memory may include, but is not limited to, a non-transitory computer-readable medium, such as flash memory, a random access memory (RAM), read-only memory (ROM), erasable programmable read-only memory (EPROM), electrically erasable programmable read-only memory (EEPROM), and non-volatile RAM (NVRAM). As used herein, the term "non-transitory computer-readable media" is intended to be representative of any tangible, computer-readable media, including, without limitation, non-transitory computer storage devices, including, without limitation, volatile and non-volatile media, and removable and non-removable media such as a firmware, physical and virtual storage, CD-ROMs, DVDs, and any other digital source such as a network or the Internet, as well as yet to be developed digital means, with the sole exception being a transitory, propagating signal. Alternatively, a floppy disk, a compact disc—read only memory (CD-ROM), a magneto-optical disk (MOD), a digital versatile disc (DVD), or any other computer-based device implemented in any method or technology for short-term and long-term storage of information, such as, computer-readable instructions, data structures, program modules and sub-modules, or other data may also be used. Therefore, the methods described herein may be encoded as executable instructions, e.g., "software" and "firmware," embodied in a non-transitory computer-readable medium. Further, as used herein, the terms "software" and "firmware" are interchangeable, and include any computer program stored in memory for execution by personal computers, workstations, clients and servers. Such instructions, when executed by a processor, cause the processor to perform at least a portion of the methods described herein. The systems and methods described herein are not limited to the specific embodiments described herein, but rather, components of the systems and/or steps of the methods may be utilized independently and separately from other components and/or steps described herein.

As will be appreciated based upon the disclosure herein, the above-described aspects of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

Embodiments of the disclosure may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein. Aspects of the disclosure may also be practiced in distributed computing environments where tasks are performed by remote processing devices that are linked through a communications network. In a distributed computing environment, program modules may be located in both local and remote computer storage media including memory storage devices.

The computer systems, computing devices, and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on vehicle or mobile devices, or associated with smart infrastructure or remote servers), and/or via computer executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. In some aspects, data inputs may include certain ML outputs.

In some aspects, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, and reinforcement learning.

In one aspect, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function that maps outputs to inputs, and utilize the predictive function to generate ML outputs based on data inputs. The example inputs and example outputs of the training data may include any of the data inputs or ML outputs described above. For example, a ML module may receive training data, generate a model that generates a ML output comprising a prediction for subsequently received data inputs.

In another aspect, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship. In one aspect, a ML module receives unlabeled data, and the ML module employs an unsupervised learning method such as "clustering" to identify patterns and organize the unlabeled data into meaningful groups. The newly organized data may be used, for example, to extract further information.

In yet another aspect, ML methods and algorithms are directed toward reinforcement learning, which involves optimizing outputs based on feedback from a reward signal. Specifically ML methods and algorithms directed toward reinforcement learning may receive a user-defined reward signal definition, receive a data input, utilize a decision-making model to generate a ML output based on the data input, receive a reward signal based on the reward signal definition and the ML output, and alter the decision-making model so as to receive a stronger reward signal for subsequently generated ML outputs. The reward signal definition may be based on any of the data inputs or ML outputs described above. In one aspect, a ML module implements reinforcement learning in a user recommendation application. The ML module may utilize a decision-making model to generate a ranked list of options based on user information received from the user and may further receive selection data based on a user selection of one of the ranked options. A reward signal may be generated based on comparing the selection data to the ranking of the selected option. The ML module may update the decision-making model such that subsequently generated rankings more accurately predict a user selection.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities and properties of components used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) are construed to cover both the singular and the plural, unless specifically noted otherwise. In some embodiments, the term "or" as used herein, including the claims, is used to mean "and/or" unless explicitly indicated to refer to alternatives only or to refer to the alternatives that are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and may also cover other unlisted steps. Similarly, any composition or device that "comprises," "has" or "includes" one or more features is not limited to possessing only those one or more features and may cover other unlisted features.

All methods described herein are performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member is referred to and claimed individually or in any combination with other members of the group or other elements found herein. One or more members of a group are included in, or deleted from, a group for reasons of convenience or patentability. When any such inclusion or deletion occurs, the specification is herein deemed to contain the group as modified thus fulfilling the written description of all Markush groups used in the appended claims.

To facilitate the understanding of the embodiments described herein, a number of terms are defined below. The terms defined herein have meanings as commonly understood by a person of ordinary skill in the areas relevant to the present disclosure. Terms such as "a," "an," and "the" are not intended to refer to only a singular entity, but rather include the general class of which a specific example may be used for illustration. The terminology herein is used to describe specific embodiments of the disclosure, but their usage does not delimit the disclosure, except as outlined in the claims.

All of the compositions and/or methods disclosed and claimed herein may be made and/or executed without undue experimentation in light of the present disclosure. While the compositions and methods of this disclosure have been described in terms of the embodiments included herein, it will be apparent to those of ordinary skill in the art that variations may be applied to the compositions and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of determining a molecular structure of a compound, the method comprising:
   obtaining a known molecular formula of the compound based on at least one of an observed spectrum and stoichiometric calculations;
   determining edges that meet per-vertex constraints of the molecular formula by using a trained deep neural network to sequentially place new edges until a candidate structure is complete, wherein the trained deep neural network is trained with training pairs generated from known molecules with observed properties and deleted edges;
   generating a plurality of candidate structures based on the determined edges;
   evaluating the plurality of candidate structures; and
   determining one candidate structure of the plurality of candidate structures as the molecular structure of the compound based on the evaluation of the plurality of candidate structures.

2. The method of claim 1, wherein obtaining the known molecular formula comprises obtaining per-vertex information from at least one of chemical shift data associated with the compound and peak splitting data.

3. The method of claim 1, wherein evaluating the plurality of candidate structures comprises determining a predicted spectrum for each candidate structure of the plurality of candidate structures.

4. The method of claim 3, wherein evaluating the plurality of candidate structures comprises calculating, for each candidate structure, a difference between the predicted spectrum for the candidate structure and the observed spectrum.

5. The method of claim 1, wherein the observed spectrum is selected as one of a nuclear magnetic resonance (NMR) spectrum, a mass-spec spectrum, an infrared (IR) spectrum, and an ultraviolet visible (UV-vis) spectrum.

6. The method of claim 1, further comprising training the deep neural network using imitation learning.

7. The method of claim 1, wherein obtaining a known molecular formula of the compound based on at least one of an observed spectrum and stoichiometric calculations comprises obtaining a known molecular formula of the compound based on the observed spectrum.

8. A computing device system for determining a molecular structure of a compound, the computing device comprising a processor and a memory, the memory containing instructions that program the processor to:
   obtain a known molecular formula of the compound based on an observed spectrum of the compound;
   determine edges that meet per-vertex constraints of the molecular formula by using a trained deep neural network to sequentially place new edges until a candidate structure is complete, wherein the trained deep neural network is trained with training pairs generated from known molecules with observed properties and deleted edges;
   generate a plurality of candidate structures based on the determined edges;
   evaluate the plurality of candidate structures; and
   determine one candidate structure of the plurality of candidate structures as the molecular structure of the compound based on the evaluation of the plurality of candidate structures.

9. The computing device of claim 8, wherein the memory contains instructions that program the processor to obtain the known molecular formula by obtaining per-vertex information from at least one of chemical shift data associated with the compound and peak splitting data.

10. The computing device of claim 8, wherein the memory contains instructions that program the processor to evaluate the plurality of candidate structures by determining a predicted spectrum for each candidate structure of the plurality of candidate structures.

11. The computing device of claim 10, wherein the memory contains instructions that program the processor to evaluate the plurality of candidate structures by calculating, for each candidate structure, a difference between the predicted spectrum of the candidate structure and the observed spectrum.

12. The computing device of claim 8, wherein the observed spectrum is selected as one of a nuclear magnetic resonance (NMR) spectrum, a mass-spec spectrum, an infrared (IR) spectrum, and an ultraviolet visible (UV-vis) spectrum.

13. The computing device of claim 8, wherein the memory contains instructions that program the processor to train the deep neural network using imitation learning.

14. The computing device of claim 8, wherein the memory contains instructions that program the processor to obtain a known molecular formula of the compound based on at least one of an observed spectrum and stoichiometric calculations by obtaining a known molecular formula of the compound based on the observed spectrum.

15. A system for determining a molecular structure of a compound, the system comprising:
  a spectroscopic instrument configured to generate an observed spectrum of the compound; and
  a computing device communicatively coupled to the spectroscopic instrument, the computing device comprising a processor and a memory, the memory containing instructions that program the processor to:
  obtain a known molecular formula of the compound based on an observed spectrum of the compound;
  determine edges that meet per-vertex constraints of the molecular formula by using a trained deep neural network to sequentially place new edges until a candidate structure is complete, wherein the trained deep neural network is trained with training pairs generated from known molecules with observed properties and deleted edges;
  generate a plurality of candidate structures based on the determined edges;
  evaluate the plurality of candidate structures; and
  determine one candidate structure of the plurality of candidate structures as the molecular structure of the compound based on the evaluation of the plurality of candidate structures.

16. The system of claim 15, wherein the memory contains instructions that program the processor to obtain the known molecular formula by obtaining per-vertex information from at least one of chemical shift data associated with the compound and peak splitting data.

17. The system of claim 15, wherein the memory contains instructions that program the processor to evaluate the plurality of candidate structures by determining a predicted spectrum for each candidate structure of the plurality of candidate structures.

18. The system of claim 17, wherein the memory contains instructions that program the processor to evaluate the plurality of candidate structures by calculating, for each candidate structure, a difference between the predicted spectrum of the candidate structure and the observed spectrum.

19. The system of claim 15, wherein the spectroscopic instrument generates the observed spectrum as one of a nuclear magnetic resonance (NMR) spectrum, a mass-spec spectrum, an infrared (IR) spectrum, and an ultraviolet visible (UV-vis) spectrum.

20. The system of claim 15, wherein the memory contains instructions that program the processor to obtain a known molecular formula of the compound based on at least one of an observed spectrum and stoichiometric calculations by obtaining a known molecular formula of the compound based on the observed spectrum.

* * * * *